(12) United States Patent
Banner et al.

(10) Patent No.: US 11,524,942 B2
(45) Date of Patent: Dec. 13, 2022

(54) METABOLITES OF [3-(4-{2-BUTYL-1-[4-(4-CHLORO-PHENOXY)-PHENYL]-1H-IMIDAZOL-4 YL}-PHENOXY)-PROPYL]-DIETHYL-AMINE

(71) Applicant: vTv Therapeutics LLC, High Point, NC (US)

(72) Inventors: William Kenneth Banner, Greensboro, NC (US); Bapu Gaddam, Ellicott City, MD (US); Dharma Rao Polisetti, High Point, NC (US); Robert Carl Andrews, Jamestown, NC (US); Samuel Victory, Winston-Salem, NC (US)

(73) Assignee: VTV THERAPEUTICS LLC, High Point, NC (US)

(*) Notice: Subject to any disclaimer, the term of this patent is extended or adjusted under 35 U.S.C. 154(b) by 0 days.

(21) Appl. No.: 17/211,942

(22) Filed: Mar. 25, 2021

(65) Prior Publication Data
US 2021/0214314 A1 Jul. 15, 2021

Related U.S. Application Data

(63) Continuation of application No. PCT/US2019/054928, filed on Oct. 7, 2019.

(60) Provisional application No. 62/828,026, filed on Apr. 2, 2019, provisional application No. 62/743,757, filed on Oct. 10, 2018.

(51) Int. Cl.
C07D 233/64 (2006.01)

(52) U.S. Cl.
CPC .................. C07D 233/64 (2013.01)

(58) Field of Classification Search
CPC .................................................. C07D 233/64
See application file for complete search history.

(56) References Cited

U.S. PATENT DOCUMENTS

| | | | |
|---|---|---|---|
| 4,265,874 A | 5/1981 | Bonsen et al. |
| 4,356,108 A | 10/1982 | Schwab et al. |
| 5,011,849 A | 4/1991 | Gassner et al. |
| 5,166,214 A | 11/1992 | Billheimer et al. |
| 5,550,833 A | 8/1996 | Fujisawa |
| 5,585,344 A | 12/1996 | Vlassara et al. |
| 5,817,826 A | 10/1998 | Ohtani et al. |
| 5,840,294 A | 11/1998 | Kisilevsky et al. |
| 5,864,018 A | 1/1999 | Morser et al. |
| 5,922,770 A | 7/1999 | Peschke et al. |
| 5,939,526 A | 8/1999 | Gaugler et al. |
| 5,962,535 A | 10/1999 | Miyamoto et al. |
| 6,221,887 B1 | 4/2001 | Asghar et al. |
| 6,268,479 B1 | 7/2001 | Stern et al. |
| 6,323,218 B1 | 11/2001 | Bush et al. |
| 6,441,049 B2 | 8/2002 | Reitz et al. |
| 6,613,801 B2 | 9/2003 | Mjalli et al. |
| 6,677,299 B2 | 1/2004 | Stern et al. |
| 6,825,164 B1 | 11/2004 | Stern et al. |
| 6,825,184 B2 | 11/2004 | Cirillo et al. |
| 7,067,554 B2 | 6/2006 | Mjalli et al. |
| 7,087,832 B2 | 8/2006 | Scher et al. |
| 7,329,884 B2 | 2/2008 | Kondo et al. |
| 7,361,678 B2* | 4/2008 | Mjalli ............... C07D 233/64 514/397 |
| 7,381,678 B2 | 6/2008 | Filimonov et al. |
| 7,421,177 B2 | 9/2008 | Schmid et al. |
| 7,423,177 B2 | 9/2008 | Mjalli et al. |
| 7,714,013 B2 | 5/2010 | Mjalli et al. |
| 7,737,285 B2 | 6/2010 | Mjalli et al. |
| 7,776,919 B2 | 8/2010 | Mjalli et al. |
| 7,884,219 B2 | 2/2011 | Hari |
| 8,274,815 B2 | 9/2012 | Ichihara et al. |
| 8,372,988 B2 | 2/2013 | Hari |
| 8,472,145 B2 | 6/2013 | Ho et al. |
| 8,580,833 B2 | 11/2013 | Jones et al. |
| 9,717,710 B2 | 8/2017 | Orlandi et al. |
| 2001/0039256 A1 | 11/2001 | Stern et al. |
| 2002/0006957 A1 | 1/2002 | Mjalli et al. |
| 2002/0118725 A1 | 8/2002 | Mollenkopf |
| 2002/0122799 A1 | 9/2002 | Stern et al. |
| 2002/0193432 A1 | 12/2002 | Mjalli et al. |
| 2003/0032663 A1 | 2/2003 | M. Mjalli et al. |
| 2004/0063770 A1 | 4/2004 | Ahn et al. |
| 2004/0082542 A1 | 4/2004 | Mjalli et al. |
| 2004/0097407 A1 | 5/2004 | Mjalli et al. |
| 2005/0026811 A1 | 2/2005 | Mjalli et al. |
| 2006/0020042 A1 | 1/2006 | McDonald et al. |
| 2006/0247253 A1 | 11/2006 | Leban et al. |

(Continued)

FOREIGN PATENT DOCUMENTS

| WO | WO-9509838 A1 | 4/1995 |
|---|---|---|
| WO | WO-9728913 A1 | 8/1997 |

(Continued)

OTHER PUBLICATIONS

Amendment No. 6 to Form S-1 Registration Statement for vTv Therapeutics Inc.. Jul. 24, 2015. pp. 2-3, 84, 96-99.

(Continued)

*Primary Examiner* — Shawquia Jackson

(74) *Attorney, Agent, or Firm* — Wilson Sonsini Goodrich & Rosati

(57) ABSTRACT

The present invention relates to metabolites of [3-(4-{2-butyl-1-[4-(4-chloro-phenoxy)-phenyl]-1H-imidazol-4-yl}-phenoxy)-propyl]-diethyl-amine. These metabolites may act as RAGE antagonists. These metabolites may also be useful in assays to measure the presence or amount of one or more metabolites of the parent compound in a sample.

7 Claims, No Drawings

(56) References Cited

U.S. PATENT DOCUMENTS

| | | |
|---|---|---|
| 2007/0021386 A1 | 1/2007 | Mjalli et al. |
| 2007/0135437 A1 | 6/2007 | Benjamin et al. |
| 2009/0035302 A1 | 2/2009 | Mjalli et al. |
| 2010/0048726 A1 | 2/2010 | McDonald et al. |
| 2010/0256119 A1 | 10/2010 | Mjalli et al. |
| 2012/0088778 A1 | 4/2012 | Mjalli et al. |
| 2014/0039025 A1 | 2/2014 | Jones et al. |
| 2017/0326113 A1 | 11/2017 | Orlandi et al. |
| 2019/0142803 A1 | 5/2019 | Orlandi et al. |
| 2021/0070714 A1 | 3/2021 | Wu |

FOREIGN PATENT DOCUMENTS

| | | |
|---|---|---|
| WO | WO-9739121 A1 | 10/1997 |
| WO | WO-9739125 A1 | 10/1997 |
| WO | WO-9822138 A1 | 5/1998 |
| WO | WO-9904485 A1 | 1/1999 |
| WO | WO-9907402 A1 | 2/1999 |
| WO | WO-9918987 A1 | 4/1999 |
| WO | WO-0019994 A1 | 4/2000 |
| WO | WO-0020458 A1 | 4/2000 |
| WO | WO-0020821 A1 | 4/2000 |
| WO | WO-0112598 A2 | 2/2001 |
| WO | WO-0192210 A1 | 12/2001 |
| WO | WO-02070473 A2 | 9/2002 |
| WO | WO-02089965 A1 | 11/2002 |
| WO | WO-03075921 A2 | 9/2003 |
| WO | WO-2004087653 A2 | 10/2004 |
| WO | WO-2004110350 A2 | 12/2004 |
| WO | WO-2005000295 A1 | 1/2005 |
| WO | WO-2006124897 A2 | 11/2006 |
| WO | WO-2008067121 A2 | 6/2008 |
| WO | WO-2008123914 A1 | 10/2008 |
| WO | WO-2008153957 A1 | 12/2008 |
| WO | WO-2009107401 A1 | 9/2009 |
| WO | WO-2010126745 A1 | 11/2010 |
| WO | WO-2011041198 A1 | 4/2011 |
| WO | WO-2011103091 A1 | 8/2011 |
| WO | WO-2014055588 A1 | 4/2014 |
| WO | WO-2019190822 A1 | 10/2019 |
| WO | WO-2020076668 A1 | 4/2020 |

OTHER PUBLICATIONS

ARICEPTO package insert, Feb. 2012.
Barile et al. The RAGE Axis in Early Diabetic Retinopathy. Investigative Opththmology & Visual Science 46(8):2916-2924 (2005).
Basta et al. Advanced glycation end products and vascular inflammation: implications for accelerated atherosclerosis in diabetes. Cardiovascular Research 63:582-592 (2004).
Behl et al. Amyloid beta peptide induces necrosis rather than apoptosis. Brain Research 645:253-264 (1994).
Behl et al. Hydrogen Peroxide Mediates Amyloid beta Protein Toxicity. Cell 77:817-827 (1994).
Berge et al. Pharmaceutical Salts. Journal of Pharmaceutical Sciences 66(1):1-19 (Jan. 1977).
Bierhaus et al. Advanced Glycation End Product (AGE)-Mediated Induction of Tissue Factor in Cultured Endothelial Cells Is Dependent on RAGE. Circulation 96:2262-2271 (1997).
Bishop et al. Neural mechanisms of ageing and cognitive decline. Nature 464:529-535 (2010).
Blacker et al. Reliability and Validity of NINCDS-ADRDA Criteria for Alzheimer's Disease. Arch. Neur. 51:1198-1204 (1994).
Bonetta. Door Slams on RAGE Alzheimer Research Forum Print News. Available at http://www.alzforum.org/new/detailprint.asp?id=2960 (Nov. 9, 2011).
Bonnardel-Phu et al. Acute Modulation of Albumin Microvascular Leakage by Advanced Glycation End Products in Microcirculation of Diabetic Rats In Vivo. Diabetes 48:2052-2058 (1999).
Burstein et al. Effect of TTP488 in patients with mild to moderate Alzheimer's disease. BMC Neurology 14:12 (2014).
Burstein et al. Development of Azeliragon, an Oral Small Molecule Antagonist of the Receptor for Advanced Glycation Endproducts, for the Potential Slowing of Loss of Cognition in Mild Alzheimer's Disease. J Prev Alzheimers Dis 5(2):149-154 (2018).
Burstein et al. Evaluation of the relationship between TTP488 plasma concentration and changes in ADAS-cog relative to placebo. Poster session presented at: the Alzheimer's Association International Conference. Jul. 13-18, 2013. Boston, Massachusetts.
Byrn et al. Pharmaceutical Solids: A Strategic Approach to Regulatory Considerations. Pharmaceutical Research 12(7):945-954 (1995).
Chartier-Harlin et al. Early-onset Alzheimer's disease caused by mutations at codon 717 of the beta-amyloid precursor protein gene. Nature 353:844-846 (1991).
Checler. Processing of the beta-Amyloid Precursor Protein and Its Regulation in Alzheimer's Disease. J Neurochemistry 65(4):1431-1444 (1995).
Chitaley et al. Antagonism of Rho-kinase stimulates rat penile erection via a nitric oxide-independent pathway. Nature Medicine 7(1):119-122 (2001).
Crall et al. The Extramural and Intramural Corollary Arteries in Juvenile Diabetes Mellitus. Am J Med 64:221-230 (1978).
Deane et al. RAGE mediates amyloid-beta peptide transport across the blood-brain barrier and accumulation in brain. Nature Medicine 9:907-913 (2003).
Degenhardt et al. Chemical modification of proteins by methylglyoxal. Cell Mol. Biol. 44:1139-1145 (1998).
Donahue et al. RAGE, LRP-1, and amyloid-beta protein in Alzheimer's disease. Ada Neuropathol 112:405-415 (2006).
Dyer et al. Accumulation of Maillard reaction products in skin collagen in diabetes and aging. J. Clin. Invest. 91:2463-2469 (1993).
Dyer et al. Formation of pentosidine during nonenzymatic browning of proteins by glucose. Identification of glucose and other carbohydrates as possible precursors of pentosidine in vivo. J. Biol. Chem. 266:11654-11660 (1991).
Fang et al. RAGE-dependent signing in microglia contributes to neuroinflammation, A-beta accumulation, and impaired teaming/memory in a mouse model of Alzheimer's disease. The FASEB J 24:1043-1055 (2010).
Galasko et al. A clinic trial of an inhibitor of RAGE-A-beta interactions in Alzheimer's disease. RI clinic trial manuscript. Aug. 8, 2012.
Galasko et al. Clinical-Neuropathologic Correlations in Alzheimer's Disease and Related Dementia. Arch. Neur. 51:888-895 (1994).
Galasko et al. Clinical trial of an inhibitor of RAGE-A-beta interactions in Alzheimer disease. Neurology 82:1536-1542 (2014).
Girouard et al. Neurovascular coupling in the normal brain and in hypertension, stroke, and Alzheimer disease. J. Appl. Physiol. 100:328-335 (2006).
Golub et al. Molecular Classification of Cancer: Class Discovery and Class Prediction by Gene Expression Monitoring. Science 286:531-537 (1999).
Goova et al. Blockade of Receptor for Advanced Glycation End-Products Restores Effective Wound Healing in Diabetic Mice. Am J Pathol 159:513-525 (2001).
Haass et al. Cellular Processing of beta-Amyloid Precursor Protein and the Genesis of Amyloid beta-Peptide. Cell 75:1039-1042 (1993).
Hambly et al. Reappraisal of the role of the diabetic state in coronary artery disease. Chest 70(2):251-257 (1976).
Hammes et al. Diabetic retinopathy risk correlates with intracellular concentrations of the glycoxidation product Nepsilon-(carboxymethyl) lysine independently of glycohaemoglobin concentrations. Diabetologia 42:603-607 (1999).
Hofmann et al. RAGE mediates a novel proinflammatory axis: a central cell surface receptor forS100/calgranulin polypeptides. Cell 97:889-901 (1999).
Hori et al. The receptor for advanced glycation end products (RAGE) is a cellular binding site for amphoterin. Mediation of neurite outgrowth and co-expression of rage and amphoterin in the developing nervous system. J. Biol. Chem. 270:25752-761 (1995).
Huttunen et al. Receptor for Advanced Glycation End Products (RAGE)-mediated Neurite Outgrowth and Activation of NF-kB

(56) References Cited

OTHER PUBLICATIONS

Require the Cytoplasmic Domain of the Receptor but Different Downstream Signing Pathways. J Biol Chem 274(28):19919-19924 (1999).
Japanese Journal of Geriatrics 49(4):419-424 (2012).
Johnson et al. MDL 29311: Antioxidant With Marked Lipid- and Glucose-Lowering Activity in Diabetic Rats and Mice. Diabetes 42:1179-1186 (1993).
Kamboh. Molecular Genetics of Late-Onset Alzheimer's Disease. Annals of Human Genetics 68:381-404 (2004).
Kannel et al. Diabetes and Cardiovascular Disease: The Framingham Study. JAMA 241(19):2035-2038 (1979).
Kannel et al. Diabetes and Glucose Tolerance as Risk Factors for Cardiovascular Disease: The Framingham Study. Diabetes Care 2(2):120-126 (1979).
Kennedy et al. Familial Alzheimer's disease. Brain 116:309-324 (1993).
Kislinger et al. Receptor for Advanced Glycation End Products Mediates Inflammation and Enhanced Expression of Tissue Factor in Vasculature of Diabetic Apolipoprotein E-Null Mice. Arterioscler Thromb Vasc Biol. 21:905-910 (2001).
Kostura et al. Efficacy of RAGE antagonist in murine model of Alzheimer's disease. Poster session presented at: the Alzheimer's Association International Congress: Jul. 13-18, 2014: Cophenhagen, Denmark.
Kostura et al. Novel Bach1 Modulators Increase HM0X1 and Suppress Hypertension in the Goldblatt Model of Renovascular Hypertension, American Heart Association Scientific Sessions, Nov. 2013, Poster.
Kumar et al. RAGE at the Blood-Brain Barrier Mediates Neurovascular Dysfunction Caused by Amyloid-bet-40 Peptide. Neurosci. Program, p141 #275.19 (2000).
Lander et al. Activation of the Receptor for Advanced Glycation End Products Triggers a p21(ras)-dependent Mitogen-activated Protein Kinase Pathway Regulated by Oxidant Stress. J Biol Chem 272(28):17810-17814 (1997).
Leder et al. v-Ha-ras transgene abrogates the initiation step in mouse skin tumorigenesis: effects of phorbol esters and retinoic acid. PNAS USA 87:9178-9182 (1990).
Levy-Lahad et al. Candidate Gene for the Chromosome 1 Familial Alzheimer's Disease Locus, Science. New Series 269(5226):973-977 (1995).
Li et al. Characterization and functional analysis of the promoter of RAGE, the receptor for advanced glycation end products. J. Biol. Chem. 272:16498-16506 (1997).
Li et al. Sp1-binding elements in the promoter of RAGE are essential for amphoterin-mediated gene expression in cultured neuroblastoma cells. J. Biol. Chem. 273:30870-30878 (1998).
Lugering et al. The myeloic related protein MRP8/14 (27E10 antigen)—usefulness as a potential marker for disease activity in ulcerative colitis and putative biological function. Eur. J. Clin. Invest. 25:659-664 (1995).
Mackic et al. Human blood-brain barrier receptors for Alzheimer's amyloid-beta 1-40. Asymmetrical binding, endocytosis, and transcytosis at the apical side of brain microvascular endothelial cell monolayer. J. Clin. Invest. 102:734-743 (1998).
Mangialasche. Alzheimer's disease: clinic tris and drug development. The LANCET Neurology 9(7):702-716 (2010).
McKhann et al.: Clinical diagnosis of Alzheimer's disease: report of the NINCDS-ADRDA Work Group under the auspices of Department of Health and Human Services Task Force on Alzheimer's Disease. Neurology 34(7):939-944 (1984).
Miyata et al. beta 2-Microglobulin modified with advanced glycation end products is a major component of hemodialysis-associated amyloidosis. J. Clin. Invest. 92:1243-1252 (1993).
Miyata et al. The receptor for advanced glycation end products (RAGE) is a central mediator of the interaction of AGE-beta2microglobulin with human mononuclear phagocytes via an oxidant-sensitive pathway. Implications for the pathogenesis of dialysis-related amyloidosis J. Clin. Invest. 98:1088-1094 (1996).
Morcos et al. Activation of Tubular Epithelial Cells in Diabetic Nephropathy. Diabetes 51:3532-3544 (2002).
Morris et al. Place navigation impaired in rats with hippocampal lesions. Nature 297:681-683 (1982).
Namenda® package insert. 2007 Jan. 2011.
Neeper et al. Cloning and expression of a cell surface receptor for advanced glycosylation end products of proteins. J. Biol. Chem. 267:14998-15004 (1992).
Ohkubo et al. Studies on Cerebral Protective Agents. VII. Synthesis of Novel 4-Arylazole Derivatives with Anti-anoxic Activity, Chem. Pharm. Bull. 43(6):947-954 (1995).
Oldfield et al. Advanced glycation end products cause epithelial-myofibroblast transdifferentiation via the receptor for advanced glycation end products (RAGE). J Clin Invest 108(12):1853-1863 (2001).
Pappolla et al. The Heat Shock/Oxidative Stress Connection: Relevance to Alzheimer Disease. Mol Chem Neropathol 28:21-24 (1996).
Park et al. Suppression of accelerated diabetic atherosclerosis by the soluble receptor for advanced glycation endproducts. Nature Medicine 4(9):1025-1031 (1998).
Parkkinen et al. Amphoterin, the 30-kDa protein in a family of HMG1-type polypeptides. Enhanced expression in transformed cells, leading edge localization, and interactions with plasminogen activation. J. Biol. Chem. 268:19726-19738 (1993).
Pastor et al. Molecular Genetics of Alzheimer's Disease. Current Psychiatry Reports 6:125-133 (2004).
PCT/US2013/062964 International Search Report and Written Opinion dated Nov. 19, 2013.
PCT/US2019/022932 International Search Report and Written Opinion dated May 28, 2019.
PCT/US2019/054928 International Search Report and Written Opinion dated Nov. 21, 2019.
Perrone et al. The Complexity of Sporadic Alzheimer's Disease Pathogenesis: The Role of RAGE as Therapeutic Target to Promote Neuroprotection by Inhibiting Neurovascular Dysfunction. Int J Alzheimer's Dis 2012:734956 (2012).
Pike et al. Neurodegeneration Induced by beta-Amyloid Peptides in vitro: The Role of Peptide Assembly State. J Neurosciences 13(4):1676-1687 (1993).
Porretta et al. Chemotherapeutic agents with an imidazole moiety. III. Synthesis and microbiologic activity of new 1,4-diaryllimidazole and 1,4-pyrrolimidazolephenylene derivatives. Il Farmaco 46(7,8):913-924 (1991).
Pyorala et al. Diabetes and Atherosclerosis: An Epidemiologic View. Diabetes/Metabolism Reviews 3(2):463-524 (1987).
Ramasamy et al. Advanced glycation end products and RAGE: a common thread in aging, diabetes, neurodegeneration, and inflammation. Glycobiology 15:16R-18R (2005).
Rammes et al. Myeloid-related protein (MRP) 8 and MRP14, calcium-binding proteins of the S100 family, are secreted by activated monocytes via a novel, tubulin-dependent pathway. J. Biol. Chem. 272:9496-9502 (1997).
Ranginwala et al. Clinic Criteria for the Diagnosis of Alzheimer Disease: Still Good After I These Years. Am. J. Geriatr. Psychiatry 16(5):384-388 (2008).
Rauvala et al. Isolation and some characteristics of an adhesive factor of brain that enhances neurite outgrowth in central neurons. J. Biol. Chem. 262:16625-16635 (1987).
Reddy et al. N epsilon-(carboxymethyl)lysine is a dominant advanced glycation end product (AGE) antigen in tissue proteins. Biochem. 34:10872-10878 (1995).
Ritthaler et al. Expression of Receptors for Advanced Glycation End Products in Peripheral Occlusive Vascular Disease. Am J Pathol 146(3):688-694 (1995).
Robertson et al. Atherosclerosis in persons with Hypertension and Diabetes Mellitus. Laboratory investigation 18(5):538-551 (1968).
Rogaev et al. Familial Alzheimer's disease in kindreds with missense mutations in a gene on chromosome 1 related to the Alzheimer's disease type 3 gene. Nature 376:775-778 (1995).
Sabbagh et al. Abstract TTP488: From Futile to Fast Track. Presented at the 2015 Alzheimer's Association International Conference. Washington, DC, Jul. 2015.

(56) References Cited

OTHER PUBLICATIONS

Sabbagh et al. Abstract TTP488 Path to Registration: Leveraging Enrichment Strategies. Presented at the 2015 Alzheimer's Association International Conference. Washington. DC, Jul. 2015.

Sabbagh et al. PF-04494700, an Oral Inhibitor of Receptor for Advanced Glycation End Products (RAGE), in Alzheimer Disease. Alzheimer Dis Assoc Disord 25(3):206-12 (2011).

Sabbagh et al. Safety and efficacy results from the phase 3. multicenter, 18-month STEADFAST tri of azeliragon in participants with mild Alzheimer's disease. Presented at 2018 CTAD. Oct. 26, 2018. Barcelona, Spain.

Sabbagh et al. TTP488 Path to Registration: Leveraging Enrichment Strategies. Presented at the 2015 Alzheimer's Association International Conference. Washington, DC, Jul. 2015.

Schafer et al. The S100 family of EF-hand calcium-binding proteins: functions and pathology. Trends Biochem Sci 21:134-140 (1996).

Schleicher et al. Increased accumulation of the glycoxidation product N(epsilon)-(carboxymethyl)lysine in human tissues in diabetes and aging. J. Clin. Invest. 99 (3):457-468 (1997).

Schmidt et al. Advanced Glycation Endproducts Interacting with Their Endothelial Receptor Induce Expression of Vascular Cell Adhesion Molecule-1 (VCAM-1) in Cultured Human Endothelial Cells and in Mice. J. Clin. Invest 96:1395-1403 (1995).

Schmidt et al. Receptor for advanced glycation end products (AGEs) has a central role in vessel wall interactions and gene activation in response to circulating AGE proteins. PNAS USA 91:8807-8811 (1994).

Schmidt et al. The V-Domain of Receptor for Advanced Glycation Endproducts (RAGE) Mediates Binding of Ages: A Novel Target for Therapy of Diabetic Complications. Supplement to Circulation 96(8):Abstract No. 194 (1997).

Schmidt et al. Isolation and Characterization of Two Binding Proteins for Advanced Glycosylation End Products from Bovine Lung Which Are Present on the Endothelial Cell Surface. J Biol Chem 267(21):14987-14977 (1992).

Schmidt et al. The dark side of glucose. Nature Med. 1:1002-1004 (1995).

Selkoe. Normal and Abnormal Biology of the beta-Amyloid Precursor Protein. Annu Review of Neuroscience 17:489-517 (1994).

Selkoe. The Molecular Pathology of Alzheimer's Disease. Neuron 6:487-498 (1991).

Selkoe. Translating cell biology into therapeutic advances in Alzheimer's disease. Nature 399:A23-31 (1999).

Semprini et al. Evidence for differential S100 gene over-expression in psoriatic patients from genetically heterogeneous pedigrees. Hum. Genet. 111(4-5):310-3 (2002).

Sherrington et al. Cloning of a gene beating missense mutations in early-onset familial Alzheimer's disease. Nature 375:754-760 (1995).

Sims et al. HMGB1 and RAGE in inflammation and cancer. Annual Review of Immunology 28:367-368 (2010).

Snowdon. Healthy Aging and Dementia: Findings from the Nun Study. Annals of Intern Medicine 139(5):450-454 (2003).

Sousa et al. Interaction of the Receptor for Advanced Glycation End Products (RAGE) with Transthyretin Triggers Nuclear Transcription Factor kB (NF-kB) Activation. Laboratory Investigation 80(7): 1101-1110 (2000).

Spite et al. Novel Lipid Mediators Promote Resolution of Acute Inflammation: Impact of Aspirin and Statins. Circulation Research 107:1170-1184 (2010).

Strittmatter et al. Apolipoprotein E: High-avidity binding to beta-amyloid and increased frequency of type 4 allele in late-onset familial Alzheimer disease. PNAS USA 90:1977-1981 (1993).

Taguchi et al. Blockade of RAGE-amphoterin signalling suppresses tumour growth and metastases. Nature 405:354-360 (2000).

Takuma et al. RAGE-mediated signing contributes to intraneuronal transport of amyloid-beta and neuron dysfunction, PNAS 106(47):20021-20026 (2009).

Tanaka et al. The receptor for advanced glycation end products is induced by the glycation products themselves and tumor necrosis factor-alpha through nuclear factor-kappa B, and by 17beta-estradiol through Sp-1 in human vascular endothelial cells. J. Biol. Chem. 275:25781-25790 (2000).

Teillet et al. Food restriction prevents advanced glycation end product accumulation and retards kidney aging in lean rats. J. Am. Soc. Nephrol 11:1488-1497 (2000).

Thompson, et al. Protein Conformation Misfolding and Amyloid Formation: Characteristics of a New Class of Disorders that Include Alzheimer's and Prion Diseases. Current Medicinal Chemistry 9:1751-1762 (2002).

Vellas et al. Long-term changes in ADAS-cog: What is clinically relevant for disease modifying trails in Alzheimer? J Nutr Health Aging 11(4):338-341 (2007).

Vlassara et al. Advanced Glycation End-products and Atherosclerosis. Ann. Med. 28:419-426 (1996).

VTv Therapeutics LLC. vTv Therapeutics Announces Topline Results from Part B of Phase 3 STEADFAST Study (Jun. 12, 2018) [Press Release].

VTv Therapeutics LLC. vTv Therapeutics Announces Topline Results from the First STEADFAST Phase 3 Study Evaluating Azeliragon in People with Mild Alzheimer's Disease (Apr. 9, 2018). [Press Release].

Waller et al. Status of the coronary arteries at necropsy in diabetes mellitus with onset after age 30 years. Analysis of 229 diabetic patients with and without clinical evidence of coronary heart disease and comparison to 183 control subjects. Am J Med 69:498-506 (1980).

Wang et al. The Profile of Soluble Amyloid beta Protein in Cultured Cell Media: Detection and Quantification of Amyloid beta Protein and Variants by immunoprecipitation-Mass Spectrometry. J Biol Chem 271(50):31894-31902 (1996).

Wautier et al. Advanced glycation end products (AGES) on the surface of diabetic erythrocytes bind to the vessel wall via a specific receptor inducing oxidant stress in the vasculature: A link between surface-associated AGEs and diabetic complications. PNAS USA 91:7742-7746 (1994).

Wautier et al. Receptor-mediated endothelial cell dysfunction in diabetic vasculopathy. Soluble receptor for advanced glycation end products blocks hyperpermeability in diabetic rats. J. Clin. Invest. 97:238-243 (1995.

Wisniewski et al. Apolipoprotein E: a pathologic chaperone protein in patients with cerebral and systemic amyloid. Neuroscience Letters 135:235-238 (1992).

Yan et al. Enhanced Cellular Oxidant Stress by the Interaction of Advanced Glycation End Products with Their Receptors/Binding Proteins. J Biol Chem 269(13):9889-9897 (1994).

Yan et al. RAGE and Alzheimer's Disease: A Progression Factor for Amyloid-beta-induced Cellular Perturbation? J Alzheimer's Dis 16:833-843 (2009).

Yan et al. Amyloid-beta peptide-receptor for advanced glycation endproduct interaction elicits neuronal expression of macrophage-colony stimulating factor: a proinflammatory pathway in Alzheimer disease. PNAS USA 94:5296-5301 (1997).

Yan et al. An intracellular protein that binds amyloid-beta peptide and mediates neurotoxicity in Alzheimer's disease. Nature 389:689-695 (1997).

Yan et al. RAGE and amyloid-beta peptide neurotoxicity in Alzheimer's disease. Nature 382:685-691 (1996).

Yan et al. Receptor-dependent cell stress and amyloid accumulation in systemic amyloidosis. Nat. Med. 6:643-651 (2000).

Yankner et al. Neurotrophic and Neurotoxic Effects of Amyloid beta Protein: Revers by Tachykinin Neuropeptides. Science 250(4978):279-282 (1990).

Yeh et al. Requirement for p38 and p44/p42 Mitogen-Activated Protein Kinases in RAGE-Mediated Nuclear Factor-kB Transcription Activation and Cytokine Secretion. Diabetes 50:1495-1504 (2001).

Zimmer et al. The S100 protein family: history, function, and expression. Brain Res. Bull. 37:417-429 (1995).

\* cited by examiner

METABOLITES OF [3-(4-{2-BUTYL-1-[4-(4-CHLORO-PHENOXY)-PHENYL]-1H-IMIDAZOL-4 YL}-PHENOXY)-PROPYL]-DIETHYL-AMINE

FIELD OF THE INVENTION

The present invention relates to metabolites of [3-(4-{2-butyl-1-[4-(4-chloro-phenoxy)-phenyl]-1H-imidazol-4-yl}-phenoxy)-propyl]-diethyl-amine (also known as azeliragon). These metabolites may act as RAGE antagonists. These metabolites may also be useful in assays to measure the presence or amount of the metabolites or of the parent compound in a sample.

BACKGROUND OF THE INVENTION

The Receptor for Advanced Glycation Endproducts (RAGE) is a member of the immunoglobulin super family of cell surface molecules. Activation of RAGE in different tissues and organs leads to a number of pathophysiological consequences. RAGE has been implicated in a variety of conditions including: acute and chronic inflammation (Hofmann et al., *Cell* 97:889-901 (1999)), the development of diabetic late complications such as increased vascular permeability (Wautier et al., *J. Clin. Invest.* 97:238-243 (1995)), nephropathy (Teillet et al., *J. Am. Soc. Nephrol.* 11: 1488-1497 (2000)), atherosclerosis (Vlassara et. al., The Finnish Medical Society DUODECIM, *Ann. Med.* 28:419-426 (1996)), and retinopathy (Hammes et al., *Diabetologia* 42:603-607 (1999)). RAGE has also been implicated in Alzbeimer's disease (Yan et al., *Nature* 382: 685-691, (1996)), erectile dysfunction, and in tumor invasion and metastasis (Taguchi et al., *Nature* 405: 354-357, (2000)).

Binding of ligands such as advanced glycation endproducts (AGEs), S100/calgranulin/EN-RAGE, β-amyloid, CML ($N^\varepsilon$-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras.

MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is a target, for down-regulation of the pathophysiological changes brought about by excessive concentrations of AGEs and other ligands for RAGE.

Certain RAGE antagonists, including [3-(4-{2-butyl-1-[4-(4-chloro-phenoxy)-phenyl]-1H-imidazol-4-yl}-phenoxy)-propyl]-diethyl-amine shown below (COMPOUND I), are disclosed in U.S. Pat. No. 7,361,678.

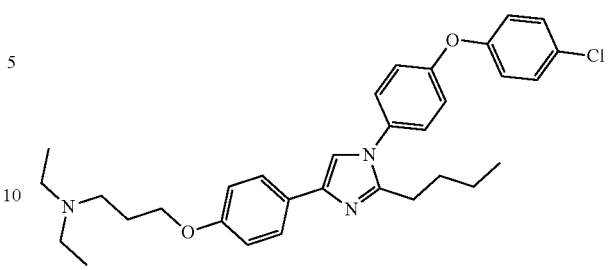

COMPOUND I

New agents that antagonize RAGE are continually needed for developing new and more effective pharmaceuticals to treat various diseases. The metabolites, compositions, and methods described herein are directed towards these and other ends.

SUMMARY OF THE INVENTION

The present invention provides a compound selected from the group consisting of:
3-(4-{2-Butyl-1-[4-(4-chloro-phenoxy)-phenyl]-1H-imidazol-4-yl}-phenoxy)-propionic acid;
[3-(4-{2-Butyl-1-[4-(4-chloro-phenoxy)-benzyl]-1H-imidazol-4-yl}-phenoxy)-propyl]-ethyl-amine;
4-{2-butyl-1-[4-(4-chloro-phenoxy)-phenyl]-1H-imidazol-4-yl}-phenol:
2-[4-[2-butyl-4-[4-[3-(diethylamino)propoxy]phenyl]imidazol-1-yl]phenoxy]-5-chloro-phenol;
5-[4-[2-butyl-4-[4-[3-(diethylamino)propoxy]phenyl]imidazol-1-yl]phenoxy]-2-chloro-phenol;
and
3-(4-{2-Butyl-1-[4-(4-chloro-phenoxy)-phenyl]-1H-imidazol-4-yl}-phenoxy)-propan-1-ol;
or a pharmaceutically acceptable salt thereof.

The present invention also provides methods of making a compound of the invention or a pharmaceutically acceptable salt thereof.

The present invention further provides pharmaceutical compositions comprising a compound of the invention or a pharmaceutically acceptable salt thereof and a pharmaceutically acceptable carrier, and methods of making thereof.

The present invention also provides methods of using a compound of the invention or a pharmaceutically acceptable salt thereof as an antagonist of RAGE or in the treatment of various medical conditions. Such diseases or disease states may include, but are not limited to, and chronic inflammation, amyloidosis, Alzheimer's disease, cancer, tumor invasion and metastasis, kidney failure, or inflammation associated with autoimmunity, inflammatory bowel disease, rheumatoid arthritis, psoriasis, multiple sclerosis, hypoxia, stroke, heart attack, hemorrhagic shock, sepsis, organ transplantation, the development of diabetic complications such as increased vascular permeability, diabetic nephropathy, diabetic retinopathy, a diabetic foot ulcer, a cardiovascular complication, diabetic neuropathy, impaired wound healing, erectile dysfunction, and osteoporosis.

The present invention also provides methods of using a compound of the invention or a pharmaceutically acceptable salt thereof in an in vitro or an in vivo assay. The in vitro or in vivo assay may be useful for measuring (either directly or indirectly) the pharmacokinetic parameters of COMPOUND I or of a compound of the invention, such as quantitating rate of absorption, quantitating the amount in tissue or plasma samples, quantitating the rate of metabolism, or quantitating the rate of excretion of COMPOUND I or a compound of the invention.

These and other embodiments of the present invention are described in greater detail in the detailed description of the invention which follows.

DETAILED DESCRIPTION

The present invention provides compounds that are metabolites of COMPOUND I, and these metabolites may bind to RAGE and have activity as RAGE antagonists. Compounds that modulate the activity of RAGE may be useful, for example, in the treatment of various diseases associated with RAGE signaling and/or inflammation cascade. The compounds of the invention may also be useful in an in vitro or in vivo assay for measuring the pharmacokinetics of COMPOUND I or of a compound of the invention. The compounds of the invention are listed in Table 1 below.

TABLE 1

| Reference | Name | Structure |
|---|---|---|
| M1 | 3-(4-{2-Butyl-1-[4-(4-chloro-phenoxy)-phenyl]-1H-imidazol-4-yl}-phenoxy)-propionic acid | 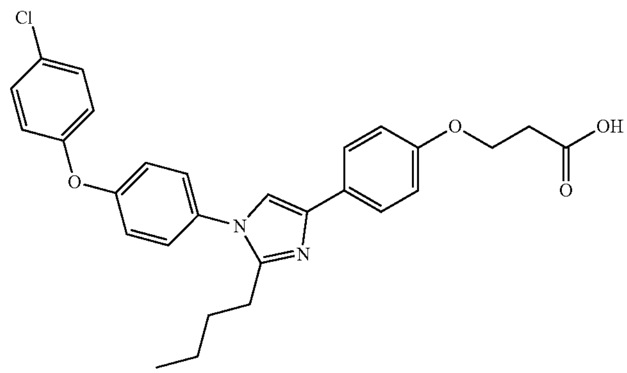 [SMILES: CCCCc1nc(-c2ccc(OCCC(=O)O)cc2)cn1-c1ccc(Oc2ccc(Cl)cc2)cc1] |
| M2 | [3-(4-{2-Butyl-1-[4-(4-chloro-phenoxy)-benzyl]-1H-imidazol-4-yl}-phenoxy)-propyl]-ethyl-amine | 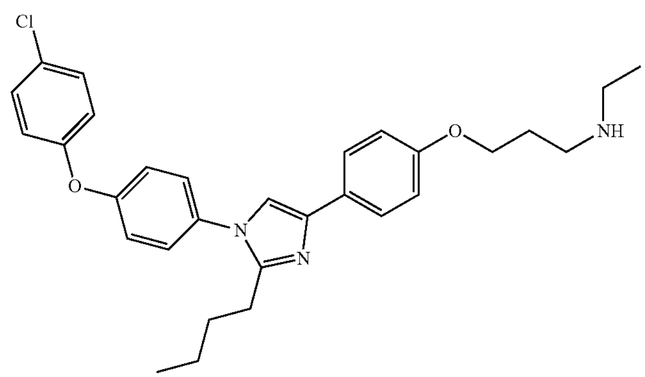 [SMILES: CCCCc1nc(-c2ccc(OCCCNCC)cc2)cn1-c1ccc(Oc2ccc(Cl)cc2)cc1] |
| M3 | 4-{2-butyl-1-[4-(4-chloro-phenoxy)-phenyl]-1H-imidazol-4-yl}-phenol | 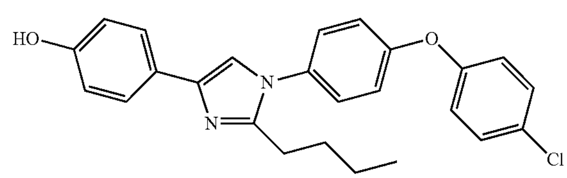 [SMILES: CCCCc1nc(-c2ccc(O)cc2)cn1-c1ccc(Oc2ccc(Cl)cc2)cc1] |
| M5 | 2-[4-[2-butyl-4-[4-[3-(diethylamino)propoxyl]phenyl]imidazol-1-yl]phenoxy]-5-chloro-phenol | 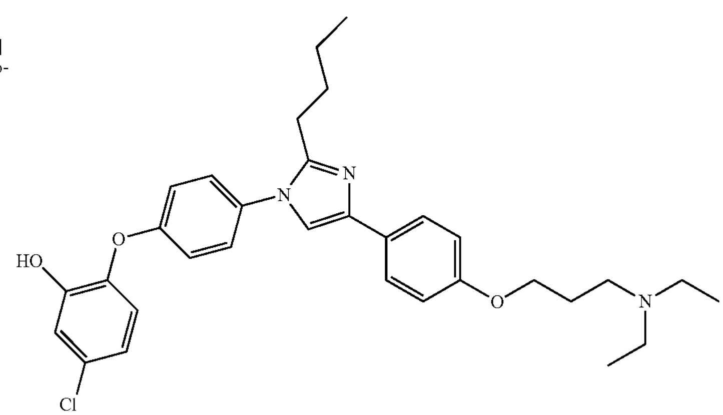 |

TABLE 1-continued

| Reference | Name | Structure |
|---|---|---|
| M6 | 5-[4-[2-butyl-4-[4-[3-(diethylamino)propoxy]phenyl]imidazol-1-yl]phenoxy]-2-chlorophenol | 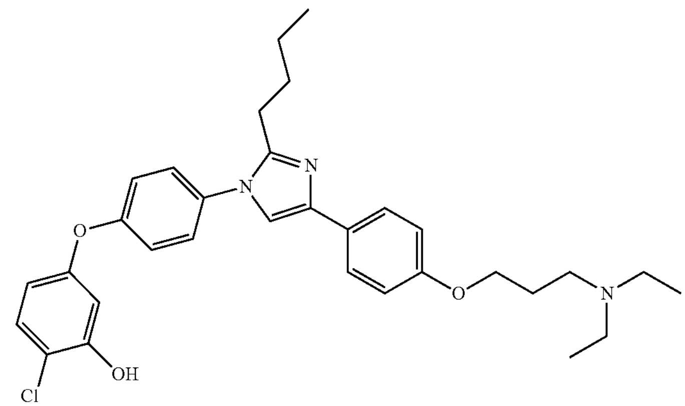 [SMILES: CCCCc1nc(-c2ccc(OCCCN(CC)CC)cc2)cn1-c1ccc(Oc2ccc(Cl)c(O)c2)cc1] |
| M7 | 3-(4-{2-Butyl-1-[4-(4-chlorophenoxy)-phenyl]-1H-imidazol-4-yl}-phenoxy)-propan-1-ol | 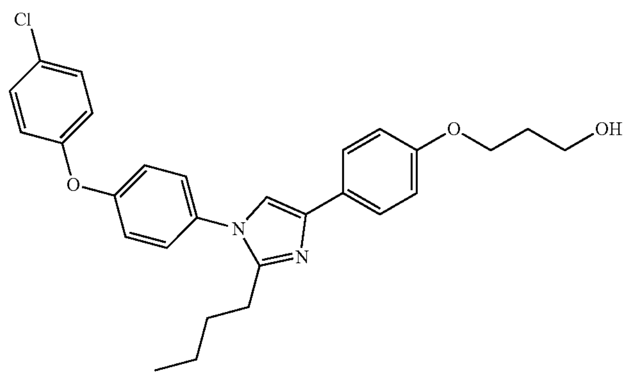 [SMILES: CCCCc1nc(-c2ccc(OCCCO)cc2)cn1-c1ccc(Oc2ccc(Cl)cc2)cc1] |

Metabolites M1, M2, M3, M5, M6 and M7 may be isolated from human plasma and/or bile taken from subjects who received one or more doses of COMPOUND I.

The binding affinity (in the form of the dissociation constant Kd) of metabolites M1, M2, M3, M5, M6 and M7 to sRAGE (the soluble extra-cellular portion of the receptor) is provided in Table 2 below. The binding affinity of a compound to sRAGE can be predictive of activity and potency of the compound as a RAGE antagonist.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Compounds of the invention also include all isotopes of atoms occurring in the metabolites. Isotopes include those atoms having the same atomic number but different mass numbers. For example, isotopes of hydrogen include tritium and deuterium.

Synthesis

Compounds of the invention, including salts thereof, can be prepared using known organic synthesis techniques and can be synthesized according to any of numerous possible synthetic routes. Example synthetic methods for preparing compounds of the invention are provided in Examples section below.

Methods of Use

The term "RAGE mediated disease" is used herein to refer to one or more conditions, diseases or disease states including, but not limited to, acute or chronic inflammation including skin inflammation such as psoriasis, rheumatoid arthritis, atopic dermatitis and lung inflammation including asthma and chronic obstructive pulmonary disease, diabetes, diabetes related complications, renal failure, hyperlipidemic atherosclerosis associated with diabetes, neuronal cytotoxicity, restenosis, Down's syndrome, dementia associated with head trauma, amyotrophic lateral sclerosis, multiple sclerosis, amyloidosis, an autoimmune disease including inflammation associated with autoimmunity or organ, tissue, or cell transplant, impaired wound healing, periodontal disease, neuropathy, neuronal degeneration, vascular permeability, nephropathy, atherosclerosis, retinopathy, Alzheimer's disease, erectile dysfunction, tumor invasion and/or metastasis, osteoporosis, and the development of diabetic late complications such as increased vascular permeability, nephropathy, retinopathy, and neuropathy.

As used herein, the phrase "a subject" refers to mammalian subjects, preferably humans, who either suffer from one or more of the aforesaid diseases or disease states or are at risk for such.

Compounds that antagonize the interaction of RAGE with its physiological ligands are potentially useful in treating diseases or conditions that may be responsive to inhibiting of the RAGE receptor. The present invention provides a method of treatment comprising: administering to a subject a compound of the invention or a pharmaceutically acceptable salt thereof. In an embodiment of this aspect, the present invention provides a method for the inhibition of the interaction of RAGE with its physiological ligands. In another embodiment of this aspect, the present invention provides a method for the inhibition RAGE signaling.

In another embodiment, the present invention provides a method for treating a RAGE mediated disease comprising administering a compound of the invention or a pharmaceutically acceptable salt thereof. In another embodiment, the present invention provides a method for treating a RAGE mediated disease comprising administering a therapeutically effective amount of a compound of the invention or a pharmaceutically acceptable salt thereof.

I. RAGE and the Complications of Diabetes

As noted above, the compounds of the present invention may be useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., J. Clin. Invest., 91:2463-2469 (1993); Reddy, S., et al., Biochem., 34:10872-10878 (1995); Dyer, D., et al., J. Biol. Chem., 266:11654-11660 (1991); Degenhardt, T., et al., Cell Mol. Biol., 44:1139-1145 (1998)). Accumulation of AGEs in the vasculature can occur focally, as in the joint amyloid composed of AGE-β2-microglobulin found in patients with dialysis-related amyloidosis (Miyata, T., et al., J. Clin. Invest., 92:1243-1252 (1993); Miyata, T., et al., J. Clin. Invest., 98:1088-1094 (1996)), or generally, as exemplified by the vasculature and tissues of patients with diabetes (Schmidt, A.-M., et al., Nature Med., 1:1002-1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., J. Biol. Chem., 272:16498-16506 (1997); Li, J., et al., J. Biol. Chem., 273:30870-30878 (1998); Tanaka, N., et al., J. Biol. Chem., 275:25781-25790(2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

II. RAGE and Cellular Dysfunction in Amyloidosis

Also as noted above, the compounds of the present invention may be useful in treating amyloidosis and/or Alzheimer's Disease. RAGE appears to be a cell surface receptor that binds β-sheet fibrillar material regardless of the composition of the subunits (amyloid-β peptide. Aβ, amylin, serum amyloid A, prion-derived peptide) (Yan, S.-D., et al., Nature, 382:685-691 (1996); Yan, S-D., et al., Nat. Med., 6:643-651 (2000)). Deposition of amyloid has been shown to result in enhanced expression of RAGE. For example, in the brains of patients with Alzheimer's disease (AD), RAGE expression increases in neurons and glia (Yan, S.-D., et al., Nature 382:685-691 (1996)). The consequences of Aβ interaction with RAGE appear to be quite different on neurons versus microglia. Whereas microglia become activated as a consequence of Aβ-RAGE interaction, as reflected by increased motility and expression of cytokines, early RAGE-mediated neuronal activation is superseded by cytotoxicity at later times. Further evidence of a role for RAGE in cellular interactions of Aβ concerns inhibition of Aβ-induced cerebral vasoconstriction and transfer of the peptide across the blood-brain barrier to brain parenchyma when the receptor was blocked (Kumar, S., et al., Neurosci. Program, p141 (2000)). Inhibition of RAGE-amyloid interaction has been shown to decrease expression of cellular RAGE and cell stress markers (as well as NF-κB activation), and diminish amyloid deposition (Yan, S-D., et al., Nat. Med., 6:643-651 (2000)) suggesting a role for RAGE-amyloid interaction in both perturbation of cellular properties in an environment enriched for amyloid (even at early stages) as well as in amyloid accumulation.

Also, it had been shown in both cellular assays and in animal studies that RAGE mediates the transcytosis of circulating Aβ across the blood-brain barrier (BBB). Such increased transcytosis of Aβ results in neuronal oxidant stress and sustained reductions in cerebral blood flow. The effects of RAGE can be inhibited by a RAGE modulator (e.g., anti-RAGE antibody or sRAGE) (see e.g., Mackic et al., J. Clin. Invest., 102:734-743 (1998); see also Kumar et al., Neurosci., Program, p 141 (2000)). These finding were confirmed by additional studies (see e.g., U.S. Pat. No. 6,825,164 at col. 17, line 48 to col. 18, line 43; Deane et al., Nature Medicine, 9:907-913 (2003)). Reduced cerebral perfusion can promote ischemic lesions which can act synergistically with Aβ to exacerbate dementia. Also, insufficient cerebral blood flow may alter Aβ trafficking across the blood brain barrier thereby reducing A clearance and promoting accumulation of Aβ in brain (see Girouard and Iadecola, J. Appl. Physiol., 100, 328-335 (2006) at page 332). Thus, the increase in cerebral blood flow promoted by RAGE antagonists may reduce the symptoms or delay onset of development of Alzheimer's Disease, or both. For example, RAGE antagonists may delay or slow loss of cognitive performance, or may improve cognitive performance of a subject suffering from dementia of Alzheimer's type, or both.

III. RAGE and Propagation of the Immune/Inflammatory Response

As noted above, the compounds of the present invention may be useful in treating inflammation. For example, S100/calgranulins have been shown to comprise a family of closely related calcium-binding polypeptides characterized by two EF-hand regions linked by a connecting peptide (Schafer, B. et al., TIBS, 21:134-140 (1996); Zimmer. D., et al., Brain Res. Bull., 37:417-429 (1995); Rammes, A., et al., J. Biol. Chem., 272:9496-9502 (1997); Lugering, N., et al., Eur. J. Clin. Invest., 25:659-664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade as implicated in the inflammatory diseases such as but not limited to rheumatoid arthritis and multiple sclerosis.

RAGE is also implicated in inflammatory diseases of the skin such as, but not limited to, atopic dermatitis, eczema, and psoriasis. Psoriasis in particular is characterized by inflamed itchy lesions. Psoriasis may be accompanied by arthropathic symptoms that are similar to those in seen in rheumatoid arthritis. There is considerable evidence that psoriasis is a polygenic autoimmune disorder. Psoriatic lesions are rich in cytokines, in particular IL-1 and IL-8, both potent proinflammatory mediators. IL-8 in particular is a chemotactic factor for neutrophils; neutrophils are also known to synthesize and secrete S100 proteins, one of the ligands for RAGE which is implicated in propagation of the immune and inflammatory response. Psoriasin, (S100A7) a new member of the S100 gene family, is a secreted protein isolated from psoriatic skin. Semprini et al. (Hum. Genet. 2002 October, 111(4-5), 310-3) have shown a linkage of psoriasis genetic susceptibility to distinct overexpression of S100 proteins in skin. Therefore, a modulator of RAGE would be expected to regulate the immune response in psoriasis.

IV. RAGE and Amphoterin

As noted above, the compounds of the present invention may be useful in treating tumor and tumor metastasis. For example, amphoterin is a high mobility group I nonhistone chromosomal DNA binding protein (Rauvala. H., et al., J. Biol. Chem., 262:16625-16635 (1987); Parkikinen, J., et al., J. Biol. Chem. 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., Nature 405:354-360 (2000)), and spontaneously arising papillomas in mice expressing the v-Ha-ras transgene (Leder. A., et al., Proc. Natl. Acad. Sci., 87:9178-9182 (1990)).

V. RAGE and Respiratory Diseases

Airway inflammation is important in the pathogenesis of asthma. Such inflammation may give rise to significant exacerbations and increases in asthma severity, as well as to be a major factor in a decline in asthmatic status. In severe exacerbations of asthma there is an intense, mechanistically heterogeneous inflammatory response involving neutrophil and eosinophil accumulation and activation. Neutrophils are a significant source of S100 proteins, key ligands for RAGE implicated in the propagation of the immune response and inflammation. Therefore, modulators of RAGE would be expected to possess therapeutic value in the treatment of asthma.

Further, the propagation step in the immune response in the lung driven by S100—RAGE interaction would be expected to lead to the activation and/or recruitment of inflammatory cells, such as neutrophils, which in chronic obstructive pulmonary diseases such as emphysema, are significant sources of damaging proteases. Therefore, a RAGE modulator would be expected possess potential in the treatment of chronic obstructive pulmonary diseases.

As used herein, the phrase "therapeutically effective amount" shall mean that amount of a drug or pharmaceutical agent that will elicit the therapeutic response of an subject that is being sought. In these methods, factors which may influence what constitutes a therapeutically effective amount include, but are not limited to, the size and weight of the subject, the biodegradability of the therapeutic agent, the activity of the therapeutic agent, the size of the effected area, as well as its bioavailability. The phrase includes amounts which, as compared to a corresponding subject who has not received such amount, results in improved treatment, healing, or amelioration of a side effect, or a decrease in the rate of advancement of a disease or disorder.

The term "treatment" as used herein, refers to the full spectrum of treatments for a given condition or disorder from which a subject is suffering, including alleviation or amelioration of one or more of the symptoms resulting from that disorder, to the delaying of the onset or progression of the disorder.

In an embodiment, the present invention provides a method for treating restenosis comprising: administering to a subject a therapeutically effective amount of a compound of the invention or a pharmaceutically acceptable salt thereof. In an embodiment, the subject is suffering from diabetes.

In an embodiment, the present invention provides a method for treating acute or chronic inflammation comprising: administering to a subject a therapeutically effective amount of a compound of the invention or a pharmaceutically acceptable salt thereof.

In an embodiment, the present invention provides a method for treating dementia associated with head trauma comprising: administering to a subject a therapeutically effective amount of a compound of the invention or a pharmaceutically acceptable salt thereof. In an embodiment, the cognitive performance of the subject is improved. In another embodiment, the cognitive performance of the subject is maintained. In another embodiment, the rate of loss of cognitive performance of the subject is slowed.

In an embodiment, the present invention provides a method for treating Alzheimer's Disease comprising: administering to a subject a therapeutically effective amount of a compound of the invention or a pharmaceutically acceptable salt thereof. With respect to Alzheimer's Disease, the present invention is believed useful in alteration the course of the underlying dementing process. Alzheimer's Disease may be diagnosed by NINCDS and DSM criteria, Mini-Mental State Examination, and Clinical Dementia Rating within particular limits. One aspect of the present invention includes improving cognitive performance comprising administering a compound of the invention or a pharmaceutically acceptable salt thereof. Cognitive performance may be assessed with the cognitive subscale of the Alzheimer's Disease Assessment Scale (ADAS-cog), as is known in the art, which scores cognitive function on a 0 to 70 scale, with higher scores indicating greater cognitive impairment. Thus, a reduction in score demonstrates cognitive improvement. One aspect of the present invention includes administering to a subject a compound of the invention or a pharmaceutically acceptable salt thereof to reduce an ADAS-cog score of a subject in need of such reduction. Such a subject may be a human be suffering from dementia of Alzheimer's type, mild to moderate Alzheimer's Diseases, or severe Alzheimer's Disease.

In addition, the progression of Alzheimer's Disease may also be assessed in a human through examination of four areas of function: General, Cognitive, Behavioral, and Activities of Daily Living. Such an assessment may be performed using a Clinician's Interview Based Impression of Change (CIBIC or CIBIC plus). One aspect of the present invention includes improvement in subject's function comprising administering a compound of the invention or a pharmaceutically acceptable salt thereof. In one embodiment, the subject's function is one or more of general, cognitive, behavioral, and activities of daily living.

In an embodiment, the present invention provides a method for improving wound healing in a diabetic subject comprising: administering to the subject a therapeutically effective amount of a compound of the invention or a pharmaceutically acceptable salt thereof, so as to improve the rate of wound healing in the subject relative to an untreated wound.

In an embodiment, the present invention provides a method for treating in a subject inflammation associated with transplantation of an organ, a tissue or a plurality of cells from a first site to a second site comprising: administering to the subject a therapeutically effective amount of a compound of the invention or a pharmaceutically acceptable salt thereof, so as to reduce inflammation in the subject. In an embodiment, the first and second sites are in different subjects. In another embodiment, the first and second sites are in the same subject. In another embodiment, the transplanted organ, cells or tissue comprise a cell or tissue of a pancreas, skin, liver, kidney, heart, bone marrow, blood, bone, muscle, artery, vein, cartilage, thyroid, nervous system, or stem cells.

Combination Therapies

In another embodiment, at least one compound of the invention or a pharmaceutically acceptable salt thereof is utilized, either alone or in combination with one or more known therapeutic agents including azeliragon or a pharmaceutically acceptable salt thereof.

In a further aspect of the present invention, the compounds of the invention may be used in adjuvant therapeutic or combination therapeutic treatments with other known therapeutic agents.

The following is a non-exhaustive listing of adjuvants and additional therapeutic agents which may be utilized in combination with a compound of the present invention:

Pharmacologic classifications of anticancer agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Metotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Anti-tumor antibodies Pharmacologic classifications of treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic classifications of treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin Pharmacologic classifications of treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In a further embodiment, the present invention provides a method of treating a RAGE mediated disease, the method comprising administering to a subject a therapeutically effective amount of a compound of the invention or a pharmaceutically acceptable salt thereof in combination with a therapeutic agent selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

In a further embodiment, the present invention provides a pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Such other therapeutic agents may be administered by a like route or different route that the compound of the invention or a pharmaceutically acceptable salt thereof. Where a compound of the invention or a pharmaceutically acceptable salt thereof is used in combination with another therapeutic agent, the composition may contain the compound of the invention or a pharmaceutically acceptable salt thereof in combination with the other therapeutic agent(s). Alternatively, where separate dosage formulations are used, the compound of the invention or a pharmaceutically acceptable salt thereof and one or more additional therapeutic agents may be administered at essentially the same time (e.g., concurrently) or at separately staggered times (e.g., sequentially).

In any of the embodiment of the above methods of treatment, the method may further comprising administering a compound of the invention or a pharmaceutically acceptable salt thereof and COMPOUND I or a pharmaceutically acceptable salt thereof. When administered together in a single dosage form or separate dosage form, the amounts of COMPOUND I or a pharmaceutically acceptable salt thereof administered per dose may be between 0.1 mg and 20 mg, and the amounts of a compound of the invention or a pharmaceutically acceptable salt thereof may be between 0.1 mg and 1,000 mg. In another embodiment, the amounts of COMPOUND I or a pharmaceutically acceptable salt thereof administered per dose may be between 0.1 mg and 20 mg, and the amounts of a compound of the invention or a pharmaceutically acceptable salt thereof may be between 0.0001% to 5%, or between 0.001% to 5% by weight relative to the amount of COMPOUND I or a pharmaceutically acceptable salt thereof or relative to the total weight of the pharmaceutical composition.

Pharmaceutical Formulations and Dosage Forms

The invention further provides pharmaceutical compositions comprising a compound of the invention or a pharmaceutically acceptable salt thereof and a pharmaceutically acceptable carrier. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, bydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or *arachis* oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, lotions, eye ointments and eye or ear drops, impregnated dressings and aerosols etc., containing the compounds of the invention are contemplated. These topical formulations may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 0.1% up to about 99% of the formulation. More usually they will form up to about 80% of the formulation. For the purpose of this application, topical applications shall include mouth washes and gargles.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Generally speaking, a compound of the invention or a pharmaceutically acceptable salt thereof may be administered at a dosage level of from about 0.003 to 500 mg/kg of the body weight of the subject being treated. In an embodiment, a compound of the invention or a pharmaceutically acceptable salt thereof may be administered at a dosage range between about 0.003 and 200 mg/kg of body weight per day, every other day, or once a week. In an embodiment, a compound of the invention or a pharmaceutically acceptable salt thereof may be administered at a dosage range between about 0.1 mg to 100 mg per day, every other day, or once a week.

The amount of active ingredient that may be combined with the carrier materials to produce a single dosage may vary depending upon the host treated and the particular mode of administration. For example, a formulation intended for oral administration to humans may contain 1 mg to 2 grams of a compound of the invention or a pharmaceutically acceptable salt thereof with an appropriate and convenient amount of carrier material which may vary from about 5 to 95 percent of the total composition. A dosage form intended for topical administration to the skin may be prepared at 0.1% to 99% compound to topical excipient ratio. A dosage form intended for inhaled administration of 0.01 to 200 mg of compound in a suitable carrier to deliver an inhaled dosage of compound. Dosage unit forms of systemically delivered compound may generally contain between from about 1 mg to about 500 mg of active ingredient. This dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination, size of effected area and the severity of the particular disease undergoing therapy.

In addition to being a metabolite of COMPOUND I, M3 has also been found to be a degradation product of COMPOUND I and/or an impurity resulting from certain methods of the synthesis of COMPOUND I. Thus, in another embodiment, the present invention provides a pharmaceutical composition comprising M3 or a pharmaceutically acceptable salt thereof and COMPOUND I or a pharmaceutically acceptable salt thereof, and a pharmaceutically acceptable carrier. In another embodiment, the present invention provides a pharmaceutical composition comprising M3 or a pharmaceutically acceptable salt thereof and COMPOUND I or a pharmaceutically acceptable salt thereof, wherein M3 or a pharmaceutically acceptable salt thereof is present in the pharmaceutical composition in an amount between 0.0001% and 5% by weight of the pharmaceutical composition. In another embodiment, M3 or a pharmaceutically acceptable salt thereof is present in the pharmaceutical composition in an amount between 0.01% and 0.5% by weight of the pharmaceutical composition. In another embodiment, a pharmaceutical composition comprises M3 or a pharmaceutically acceptable salt thereof and between 0.1 mg and 100 mg, or between 0.1 mg and 50 mg, or between 1 mg and 30 mg, or between 1 mg and 10 mg of COMPOUND I or a pharmaceutically acceptable salt thereof, wherein M3 or a pharmaceutically acceptable salt thereof is present in the pharmaceutical composition in an amount between 0.0001% and 5%, or between 0.001% and 0.01%, or between 0.01% and 1% by weight relative to the amount of COMPOUND I or a pharmaceutically acceptable salt thereof in the pharmaceutical composition or relative to the total weight of the pharmaceutical composition.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo.

The present invention further includes isotopically-labeled or isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include, but are not limited to, $^{2}H$ (also written as D for deuterium), $^{3}H$ (also written as T for tritium), and $^{14}C$. The radionuclide that is incorporated in the instant radio-labeled compounds will depend on the specific application of that radio-labeled compound.

A labeled compound of the invention can be used in a screening assay or in a toxicology or a pharmacokinetic study of COMPOUND I to identify/evaluate the absorption, distribution, metabolism, and excretion profile of COMPOUND I and/or metabolites thereof. For example, isotopically enriched forms of various metabolites may be prepared by substituting $d_9$-valeryl chloride ($CD_3CD_2CD_2CD_2COCl$) for valeryl chloride when synthesizing the metabolite, such that the butyl group of M1-M3 and M5-M7 is isotopically enriched in deuterium.

EXAMPLES

Metabolite 1 (M1): 3-(4-{2-Butyl-1-[4-(4-chloro-phenoxy)-phenyl]-1H-imidazol-4-yl}-phenoxy)-propionic acid

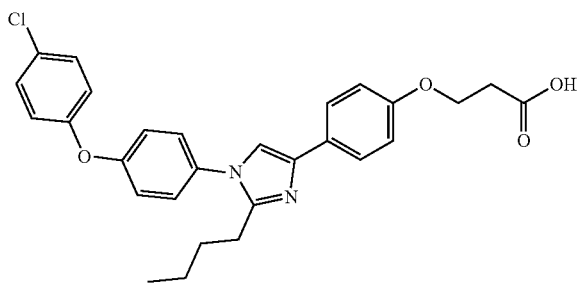 [SMILES: CCCCc1nc(-c2ccc(OCCC(=O)O)cc2)cn1-c1ccc(Oc2ccc(Cl)cc2)cc1]

To 4-{2-butyl-1-[4-(4-chloro-phenoxy)-phenyl]-1H-imidazol-4-yl}-phenol (5.5 g) (See U.S. Pat. Nos. 7,361,678 and 8,580,833) in t-butyl acrylate (50 mL) was added DBU (1 equivalent), and the mixture was heated at 100° C. for 3 hr. The reaction mixture was concentrated, and a water (100 mL) and 1:1 ethyl acetate-hexanes mixture (100 mL) was added. The mixture was stirred for 30 minutes and filtered. The organic layer was isolated and concentrated. The residue was purified by column chromatography on silica gel using 1-100% ethyl acetate in hexanes as eluent. The desired fractions were concentrated, and the residue was co-evaporated with n-heptane to obtain tert-butyl 3-[4-[2-butyl-1-[4-(4-chlorophenoxy)phenyl]imidazol-4-yl]phenoxy]propanoate (1.4 g). The ester was dissolved in 4 N HCl in dioxane. Water (5 mL) was added, and the mixture was stirred for 30 minutes. The resulting solution was concentrated and dried to obtain 3-(4-{2-butyl-1-[4-(4-chloro-phenoxy)-phenyl]-1H-imidazol-4-yl}-phenoxy)-propionic acid as solid.

$^1$H NMR (DMSO-d$_6$, TMS): δ 0.82 (t, 3H), 1.25 (m, 2H), 1.59 (m, 2H), 2.75 (t, 2H), 2.92 (m, 2H), 4.22 (t, 2H), 7.12-7.20 (m, 4H), 7.29 (d, 2H), 7.55 (d, 2H), 7.75 (d, 2H), 7.92 (d, 2H), 8.21 (s, 1H), ppm.

Metabolite 2 (M2): [3-(4-{2-Butyl-1-[4-(4-chloro-phenoxy)-benzyl]-1H-imidazol-4-yl}-phenoxy)-propyl]-ethyl-amine

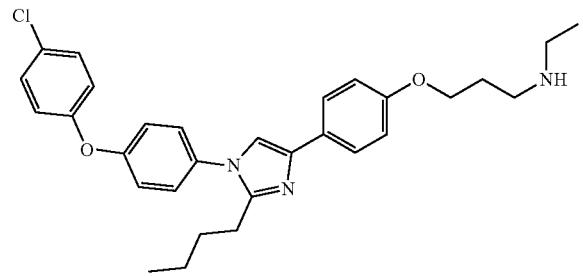 [SMILES: CCCCc1nc(-c2ccc(OCCCNCC)cc2)cn1-c1ccc(Oc2ccc(Cl)cc2)cc1]

[3-(4-{2-Butyl-1-[4-(4-chloro-phenoxy)-benzyl]-1H-imidazol-4-yl}-phenoxy)-propyl]-diethyl-amine (18 g) (See U.S. Pat. No. 7,361,678) was dissolved in anhydrous dichloromethane (150 mL) in a 3-neck round bottom flask under nitrogen. The contents were cooled to −78° C., and a solution of (1-chloroethyl)-chloroformate (100 g) in dichloromethane (150 mL) was added dropwise over 0.5 hour. The contents were allowed to warm up to room temperature and stirred for 16 hours at that temperature. All the volatiles were evaporated on a rotavapor under reduced pressure. Water (150 mL) and ethyl acetate were added, and the pH was adjusted to about 12 using 5 N sodium hydroxide with stirring. The layers were separated, and the organic layer was dried over sodium sulfate and concentrated. The residue was purified by column chromatography on silica gel using 5-15% methanol in dichloromethane as eluent. The desired fractions were concentrated and the residue was co-evaporated with n-heptane to obtain [3-(4-{2-Butyl-1-[4-(4-chloro-phenoxy)-benzyl]-1H-imidazol-4-yl}-phenoxy)-propyl]-ethyl-amine as solid (7.8 g).

$^1$H NMR (CDCl$_3$, TMS): δ 0.82 (t, 3H), 1.15 (t, 3H), 1.35 (m, 3H), 1.65 (m, 2H), 1.95 (m, 2H), 2.65 (m, 4H), 2.8 (t, 2H), 4.05 (t, 2H), 6.9 (d, 2H), 7.05 (d, 2H), 7.1 (d, 2H), 7.17 (s, 1H), 7.25 (d, 2H), 7.35 (d, 2H), 7.75 (d, 2H) ppm.

Metabolite 3 (M3): 4-{2-butyl-1-[4-(4-chloro-phenoxy)-phenyl]-1H-imidazol-4-yl}-phenol

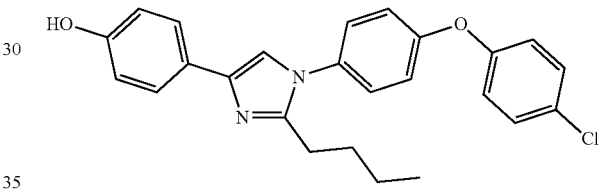

See Intermediate A1 in U.S. Pat. No. 8,580,833.

Metabolite 5 (M5): 2-[4-[2-butyl-4-[4-[3-(diethyl-amino)propoxy]phenyl]imidazol-1-yl]phenoxy]-5-chloro-phenol

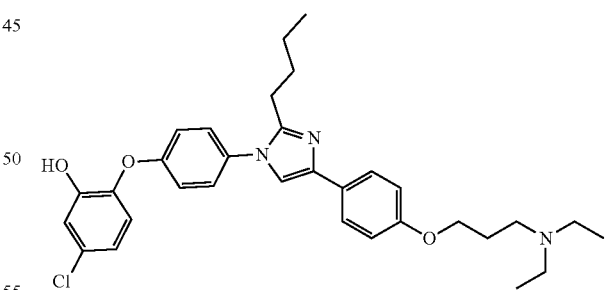

N-[4-[4-chloro-2-[(4-methoxyphenyl)methoxy]phenoxy]phenyl]-N-[2-(4-hydroxyphenyl)-2-oxo-ethyl]pentanamide (1.3 g) was prepared from 4-acetoxyacetophenone, 4-[4-chloro-2-[(4-methoxyphenyl)methoxy]phenoxy]aniline and valeroyl chloride using previously described procedures (See U.S. Pat. Nos. 7,361,678 and 8,580,833) and converted to N-[4-[4-chloro-2-[(4-methoxyphenyl)methoxy]phenoxy]phenyl]-N-[2-[4-[3-(diethylamino)propoxy]phenyl]-2-oxo-ethyl]pentanamide (0.8 g) by treating with 3-(diethylamino)propan-1-ol, triphenylphospine and DIAD in dichloromethane followed by column purification on silica using 0-15% methanol in dichloromethane as eluent.

N-[4-[4-chloro-2-[(4-methoxyphenyl)methoxy]phenoxy] phenyl]-N-[2-[4-[3-(diethylamino)propoxy]phenyl]-2-oxo-ethyl]pentanamide (0.8 g) was converted to 2-[4-[2-butyl-4-[4-[3-(diethylamino)propoxy]phenyl]imidazol-1-yl] phenoxy]-5-chloro-phenol (1.2 g) by treating with ammonium acetate in acetic acid at 100-110° C. for 48 h using procedure described previously. (See U.S. Pat. No. 7,361,678).

$^1$H NMR (CDCl$_3$, TMS): δ 0.65 (t, 3H), 1.25 (t, 6H), 1.25 (m, 2H), 1.65 (m, 2H), 1.95 (s, 1H), 2.05 (m, 2H), 2.52 (m, 2H), 2.75-2.9 (m, 6H), 3.92 (t, 2H), 6.85-6.92 (m, 4H), 7.02-7.12 (m, 4H), 7.2 (d, 2H), 7.64 (d, 2H) ppm.

Metabolite 6 (M6): 5-[4-[2-butyl-4-[4-[3-(diethyl-amino)propoxy]phenyl]imidazol-1-yl]phenoxy]-2-chloro-phenol

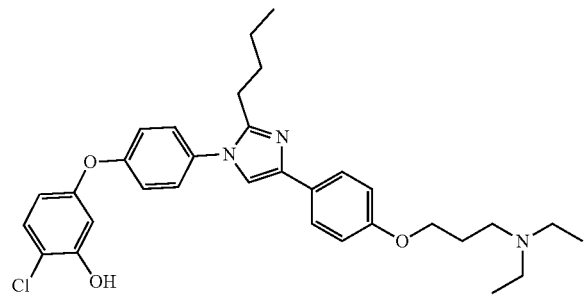 [SMILES: CCCCc1nc(-c2ccc(OCCCN(CC)CC)cc2)cn1-c1ccc(Oc2ccc(Cl)c(O)c2)cc1]

N-[4-[4-chloro-3-[(4-methoxyphenyl)methoxy]phenoxy] phenyl]-N-[2-(4-hydroxyphenyl)-2-oxo-ethyl]pentanamide (5.36 g) is prepared from 4-acetoxyacetophenone, 4-[4-chloro-3-[(4-methoxyphenyl)methoxy]phenoxy]aniline and valeroyl chloride using previously described procedures (See U.S. Pat. Nos. 7,361,678 and 8,580,833) and converted to N-[4-[4-chloro-3-[(4-methoxyphenyl)methoxy]phenoxy] phenyl]-N-[2-[4-[3-(diethylamino)propoxy]phenyl]-2-oxo-ethyl]pentanamide (5.1 g) by treating with 3-(diethylamino) propan-1-ol, triphenylphospine and DIAD in dichloromethane followed by column purification on silica using 0-15% methanol in dichloromethane as eluent.

N-[4-[4-chloro-3-[(4-methoxyphenyl)methoxy]phenoxy] phenyl]-N-[2-[4-[3-(diethylamino)propoxy]phenyl]-2-oxo-ethyl]pentanamide (5.1 g) was converted to 5-[4-[2-butyl-4-[4-[3-(diethylamino)propoxy]phenyl]imidazol-1-yl] phenoxy]-2-chloro-phenol (1.2 g) by treating with ammonium acetate in acetic acid at 100-110° C. for 48 hr using procedure described previously. (See U.S. Pat. No. 7,361,678).

$^1$H NMR (CDCl$_3$, TMS): δ 0.65 (t, 3H), 1.2 (t, 6H), 1.25 (t, 2H), 1.65 (m, 2H), 2.0 (m, 2H), 2.6-2.75 (m, 8H), 3.2 (br, 1H), 4.05 (t, 2H), 6.56 (m, 1H), 6.7 (m, 1H), 6.88 (d, 2H), 7.04 (m, 3H), 7.25 (d, 2H), 7.3 (d, 1H), 7.66 (d, 2H) ppm.

Metabolite 7 (M7): 3-(4-{2-Butyl-1-[4-(4-chloro-phenoxy)-phenyl]-1H-imidazol-4-yl}-phenoxy)-propan-1-ol

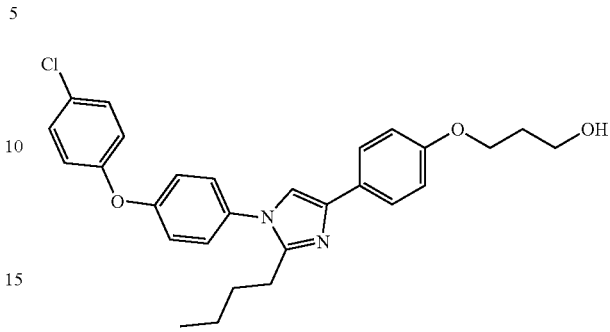

A mixture of 4-{2-butyl-1-[4-(4-chloro-phenoxy)-phenyl]-1H-imidazol-4-yl}-phenol (3 g) (See U.S. Pat. Nos. 7,361,678 and 8,580,833), 3-chloropropanol and potassium carbonate in acetone (50 mL) was heated at reflux for 3 days. The reaction mixture was filtered, and concentrated, and the residue was purified by column chromatography on silica gel using 1-100% ethyl acetate in hexanes as eluent. The desired fractions were concentrated, and the residue was recrystallized from ethyl acetate and hexanes to obtain 3-(4-{2-Butyl-1-[4-(4-chloro-phenoxy)-phenyl]-1H-imidazol-4-yl}-phenoxy)-propan-1-ol (2.7 g) as a white solid.

$^1$H NMR (CDCl$_3$, TMS): δ 0.85 (t, 3H), 1.32 (m, 2H), 1.65 (m, 2H), 1.8 (br, 1H), 2.05 (m, 2H), 2.65 (m, 2H), 3.78 (m, 2H), 4.25 (t, 2H), 6.92 (d, 2H), 7.02 (d, 2H), 7.08 (d, 2H), 7.03 (s, 1H), 7.29 (d, 2H), 7.35 (d, 2H), 7.71 (d, 2H) ppm.

Metabolism Studies of COMPOUND I

Assessments of the metabolism of COMPOUND I was conducted using human plasma and bile samples taken from subjects who received doses of COMPOUND I. The study was a multiple dose trial evaluating eight healthy individuals receiving COMPOUND I orally for 14 days. Subjects received a loading dose of 15 mg once daily for 6 days and then a daily maintenance dose of 5 mg for 8 days. Plasma samples were taken predose on Day 1. Plasma was also collected prior to dosing on Days 11, 12, and 13. In addition, plasma was collected on Day 14 at 0, 1, 2, 4, 6, 8, 10 hours postdose and at 24 and 28 hours postdose on Day 15. Bile samples were collected on Day 15 (28 hours post dose) for up to 4 hours by continuous suction through an oroenteric tube placed fluoroscopically near the bile duct. Bile was collected in the following fractions: 0-0.5 hours after start of bile collection (approximately 24-24.5 hours after COMPOUND I administration), 0.5-1.0, 1.0-2.0, 2.0-3.0, and 3.0-4.0 hours after start of bile collection.

One assay method to determine the concentrations of COMPOUND I and certain metabolites in human plasma is as follows. Concentrations of COMPOUND I and certain metabolites in human plasma may be measured using assays based on protein precipitation followed by high-performance liquid chromatography and tandem mass spectrometry (HPLC-MS/MS) with a lower limit of quantitation of 0.2 ng/mL or 0.4 ng/mL for each analyte. An internal standard compound of deuterated (d9) COMPOUND I, M1. M2, M3, M5, M6 or M7 may be used to prepare an internal standard solution (0.5 mg/mL in methanol-DMSO, 90:10 v/v). An aliquot of 50 μL of K$_2$EDTA plasma is added to a 2 mL 96 DeepWell® plate containing 450 μL or blank solvent (acetonitrile containing 0.2% formic acid, v/v) and 450 µL of internal standard. Plates are vortexed at 1000 rpm for at least 5 minutes followed by centrifugation at approximately 4000 rpm for at least 5 minutes at room temperature. An aliquot of 100 µL of supernatant is transferred into either a 1 mL or 500 µL DeepWell® plate pre-filled with 100 µL of reconstitution solution (water-formic acid, 100:0.2 v/v). Plates are vortexed at approximately 1000 rpm for at least 5 minutes before loading to the HPLC-MS/MS system for analysis. The HPLC conditions are as follows: column. XBridge (Waters) C18, 3.5 µM, 2.1×50 mm; column temperature, 45° C.; mobile phase composition, mobile phase A: 0.1% formic acid and 0.05% trifluoroacetic acid (v/v/v), mobile phase B: acetonitrile containing 0.1% formic acid and 0.05% trifluoroacetic acid (v/v/v); % mobile phase A to % mobile phase B varied from 65%/35% to 5%/95% over the 12 minute run time; flow rate, 1 mL/min. Plasma quality control samples are analyzed at low, mid, and high concentrations in each analytical batch. Similar methods may be used to assay bile samples.

Microscale Thermophoresis

The binding affinity of COMPOUND I and compounds of the invention to human sRAGE (the soluble extracellular domain of the human receptor for advanced glycation endproducts) was measured using microscale thermophoresis.

Microscale Thermophoresis System (Monolith NT.115 Pico, NanoTemper, Inc) was used to determine the binding affinity of COMPOUND I and metabolites M1, M2, M3, M5, M6 and M7 to recombinant human sRAGE. sRAGE was labeled with NT-647-NHS fluorescence dye. Around 5 nM sRAGE was subsequently added to compounds at concentrations from 600 nM to 20 pM and incubated for 5 minutes at 25° C. in buffer containing 25 mM Hepes (pH 7.5), 5 mM $CaCl_2$), 5 mM $MgCl_2$, 50 mM NaCl, 0.05% Tween20 and 1% DMSO before proceeding to microscale thermophoresis.

The raw thermophoresis data and average Kds were generated according to manufacturer's protocol using the Microscale Thermophoresis System analysis software.

The average Kd between recombinant human sRAGE and COMPOUND I, M1-M3, M5, M6 or M7 is shown in the table below.

TABLE 2

| Compound | Average Kd (nM) |
| --- | --- |
| COMPOUND I | 12.7 |
| M1 | 219 |
| M2 | 22.3 |
| M3 | 257 |
| M5 | 9.7 |
| M6 | 9.8 |
| M7 | 99.8 |

S100B and Amyloid Beta ELISA Assay

The following assay method may be used to identify compounds that may be useful as inhibitors of binding of physiological RAGE ligands, such as S100b and β-amyloid, to RAGE.

S100b or β-amyloid (500 ng/100 µL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 5 mM $CaCl_2/MgCl_2$) containing 1% bovine serum albumin (BSA) (300 µL/well) for 1 h at room temperature. The wells are aspirated.

Test compounds are dissolved in nanopure water (concentration: 10-100 µM). DMSO may be used as co-solvent. 25 µL of test compound solution in 4% DMSO is added, along with 75 µL sRAGE (6 nM FAC) to each well and samples are incubated for 1 h at 37° C. The wells are washed several times with 155 mM NaCl pH 7.2 buffer saline and are soaked for several seconds between each wash.

Non-radioactive detection is performed by adding 10 µL Biotinylated goat F(ab')2 Anti-mouse IgG. (8.0×10-4 mg/mL, FAC), 5 µL Alk-phos-Streptavidin (3×10-3 mg/mL FAC), 0.42 µL per 5 mL Monoclonal antibody for sRAGE (FAC 6.0×10-3 mg/mL) to 5 mL 50 mM imidazole buffer saline (pH 7.2) containing 0.2% bovine serum albumin and 5 mM $CaCl_2$. The mixture is incubated for 30 minutes at room temperature.

100 µL of complex is added to each well and incubation is allowed to proceed at room temperature for 1 h. Wells are washed several times with wash buffer and soaked several seconds between each wash. 100 µL 1 mg/mL (pNPP) in 1 M diethanolamine (pH adjusted to 9.8 with HCl) is added. Color is allowed to develop in the dark for 30 min to 1 h at room temperature. The reaction is quenched with 10 µL of stop solution (0.5-1.0 N NaOH in 50% ethanol) and the absorbance is measured spectrophotometrically with a microplate reader at 405 nm.

Metabolite M2 was tested according to the assay method described above, employing S100b or β-amyloid as the RAGE ligand, and was found to possess IC50 shown below. IC50 (µM) in the ELISA assay represents the concentration of compound at which 50% signal has been inhibited.

| Compound | IC50 (β-amyloid) (µM) | IC50 (S100b) (µM) |
| --- | --- | --- |
| M2 | 1.23 | 1.18 |

We claim:

1. A compound selected from the group consisting of:
   3-(4-{2-butyl-1-[4-(4-chloro-phenoxy)-phenyl]-1H-imidazol-4-yl}-phenoxy)-propionic acid;
   [3-(4-{2-butyl-1-[4-(4-chloro-phenoxy)-benzyl]-1H-imidazol-4-yl}-phenoxy)-propyl]-ethyl-amine;
   2-[4-[2-butyl-4-[4-[3-(diethylamino)propoxy]phenyl]imidazol-1-yl]phenoxy]-5-chloro-phenol;
   5-[4-[2-butyl-4-[4-[3-(diethylamino)propoxy]phenyl]imidazol-1-yl]phenoxy]-2-chloro-phenol; and
   3-(4-{2-butyl-1-[4-(4-chloro-phenoxy)-phenyl]-1H-imidazol-4-yl}-phenoxy)-propan-1-ol;
   or a pharmaceutically acceptable salt thereof.

2. The compound of claim 1, wherein the compound is 3-(4-{2-butyl-1-[4-(4-chloro-phenoxy)-phenyl]-1H-imidazol-4-yl}-phenoxy)-propionic acid or a pharmaceutically acceptable salt thereof.

3. The compound of claim 1, wherein the compound is [3-(4-{2-butyl-1-[4-(4-chloro-phenoxy)-benzyl]-1H-imidazol-4-yl}-phenoxy)-propyl1-ethyl-amine or a pharmaceutically acceptable salt thereof.

4. The compound of claim 1, wherein the compound is 2-[4-[2-butyl-4-[4-[3-(diethylamino)propoxy]phenyl]imidazol-1-yl]phenoxy]-5-chloro-phenol or a pharmaceutically acceptable salt thereof.

5. The compound of claim 1, wherein the compound is 5-[4-[2-butyl-4-[4-[3-(diethylamino)propoxy]phenyl]imidazol-1-yl]phenoxy]-2-chloro-phenol or a pharmaceutically acceptable salt thereof.

6. The compound of claim 1, wherein the compound is 3-(4-{2-butyl-1-[4-(4-chloro-phenoxy)-phenyl]-1H-imidazol-4-yl}-phenoxy)-propan-1-ol or a pharmaceutically acceptable salt thereof.

7. A pharmaceutical composition comprising a compound selected from the group consisting of:
- 3-(4-{2-butyl-1-[4-(4-chloro-phenoxy)-phenyl]-1H-imidazol-4-yl}-phenoxy)-propionic acid;
- [3-(4-{2-butyl-1-[4-(4-chloro-phenoxy)-benzyl]-1H-imidazol-4-yl}-phenoxy)-propyl]-ethyl-amine;
- 2-[4-[2-butyl-4-[4-[3-(diethylamino)propoxy]phenyl]imidazol-1-yl]phenoxy]-5-chloro-phenol;
- 5-[4-[2-butyl-4-[4-[3-(diethylamino)propoxy]phenyl]imidazol-1-yl]phenoxy]-2-chloro-phenol; and
- 3-(4-{2-butyl-1-[4-(4-chloro-phenoxy)-phenyl]-1H-imidazol-4-yl}-phenoxy)-propan-1-ol;

or a pharmaceutically acceptable salt thereof, and at least one pharmaceutically acceptable carrier.

* * * * *